United States Patent [19]
Doue

[11] Patent Number: 5,361,202
[45] Date of Patent: Nov. 1, 1994

[54] COMPUTER DISPLAY SYSTEM AND METHOD FOR FACILITATING ACCESS TO PATIENT DATA RECORDS IN A MEDICAL INFORMATION SYSTEM

[75] Inventor: John C. Doue, Manchester, Mass.

[73] Assignee: Hewlett-Packard Company, Palo Alto, Calif.

[21] Appl. No.: 79,667

[22] Filed: Jun. 18, 1993

[51] Int. Cl.$^5$ ............................................. G06F 15/00
[52] U.S. Cl. ........................... 364/413.01; 364/413.04; 395/600
[58] Field of Search ...................... 364/413.01, 413.04; 395/600

[56] References Cited

U.S. PATENT DOCUMENTS

| | | | |
|---|---|---|---|
| 3,872,448 | 3/1975 | Mitchell, Jr. | 340/172.5 |
| 4,878,175 | 10/1989 | Norden-Paul et al. | 364/413.01 |
| 4,893,270 | 1/1990 | Beck et al. | 364/900 |
| 5,072,383 | 12/1991 | Brimm et al. | 364/413.2 |
| 5,077,666 | 12/1991 | Brimm et al. | 364/413.02 |
| 5,267,155 | 11/1993 | Buchanan et al. | 364/419.14 |

OTHER PUBLICATIONS

Horn et al. "Profile of Physician Practice and Patient Severity of Illness", American Journal of Public Health, May 1986.
HP CareVue 9000 Clinical Information Quick Guide, Hewlett Packard Company, 1990-1993, Version FO, pp. Contents-1 to Contents-3 and 4-1 to 4-8 (HP Part No. M1215-90123).
HP M1251A Monitoring Full Disclosure Review System, User's Guide Hewlett Packard, Aug. 1991, HP Part No. M1251-91901, pp. Contents-1, 2-1, 2-4, 2-5, 2-7 to 2-12.

Primary Examiner—Roy N. Envall, Jr.
Assistant Examiner—Frantzy Poinvil

[57] ABSTRACT

To improve access to patient information in medical information system for a health care facility, a computer display system, and a method for such a display system, includes a displayed representation of the duration of the stay of an identified patient in the health care facility. In such a medical information system patient data is stored in data files in a database, wherein each data file in the database is comprised of a plurality of data records. A user positions a cursor on the displayed representation using an input unit and signals the computer of a desired date and time. The computer, in response to the signal determines the desired date and time from the position of the cursor and accesses a data record or records from the data file based on the desired date and time. The accessed data record or records may then be displayed. The data records may be time-stamped. In that case, the duration of the patient's stay is the time period between the earliest and latest time stamps.

22 Claims, 7 Drawing Sheets

COMPUTER DISPLAY SYSTEM AND METHOD FOR FACILITATING ACCESS TO PATIENT DATA RECORDS IN A MEDICAL INFORMATION SYSTEM

FIELD OF THE INVENTION

This invention is related to computer display systems which facilitate access to patient information stored in a database of a medical information system. More particularly, the invention is related to medical information systems which facilitate access to stored, time-stamped patient data records.

BACKGROUND OF THE INVENTION

Medical information systems are commonly used by health care facilities for storing patient information, replacing, for example, paper-based flow sheets typically found at a patient bedside in most hospitals. An example of such a medical information system is the HP CareVue 9000 system available from Hewlett-Packard Company of Palo Alto, Calif.

While such systems provide highly satisfactory operation and have many advantages, a problem with current medical information systems is the speed with which a clinician may access patient data records in the system from a patient bedside. Typically, the clinician must scroll through a patient's data records in the database sequentially according to the date and time the data records were entered into the system. Where the patient has been in the hospital for a long time, review of these data records can be particularly slow. In contrast, with a paper-based chart, the clinician can simply flip through the pages of a chart. The restriction found in computerized medical information systems can be annoying to clinicians who desire much faster access to data records for a specific patient from a specific date and time.

Most tools which allow a user to access information in a computerized database are textually-based and thus require a user to enter accurately into the computer indices for the information to be retrieved. Often, these indices have special formats which need to be learned by each user. A user therefore takes more time to become familiar with such a system.

Non-textual tools for accessing information are not common in database systems. While graphical tools have been used in commercially-available word-processing, spreadsheet and graphics editing programs for navigating documents, on a line-by-line or page-by-page basis, these tools do not use the displayed data to assist in its navigation. Also, the relationship between a displayed document and any tool is fixed for all documents. For example, a vertical scroll bar in a word processor always relates to the length of the data file in a fixed manner.

The only use of a graphical navigational tool in a computer system using medical information, of which the inventors are aware at the time of filing this application, is found in the AIM product available from Hewlett-Packard Company, of Palo Alto, Calif.

The AIM product allows for receipt, storage and display of up to twenty-four hours of an arrhythmia waveform. The waveform data are stored in a linear array where each sample point is a fixed number of bytes. The time of the first sample point is stored. The time of the last sample point is determined by adding the number of samples, times the sample interval, to the start time. A bar at the bottom of the video display window representing the time between the first and last samples. By clicking on a point on the bar, the data for the corresponding time is shown by retrieving data from the corresponding location in the data file.

SUMMARY OF THE INVENTION

To improve access to patient data records in a medical information system, the present invention provides a computer display system and method wherein a representation of the duration of the patient's stay at the health care facility is displayed. This representation may be a timeline representing the time span covered by time-stamped data records in the data file for the patient.

In the invention, the duration of a patient's stay is determined based on the data records for that patient. The data records are typically independent of each other, i.e., information in different data records typically unrelated. A line, or other representation, based on this determined duration is generated and displayed. In a medical information system with time-stamped data records, the duration is determined by the time period between the first data record and either the last data record for the patient or the current time. Typically, time periods between data records are irregular. A user positions a cursor on the timeline on the display using an input unit for the computer and signals the computer of a desired date and time. The computer, in response to a signal from the input unit determines the desired date and time, and accesses at least one data record from the data file based on the desired date and time. Other data records having time stamps close to the desired date and time may also be accessed. The accessed data may then be displayed.

An embodiment of a computer display system in accordance with the invention includes a database in which there is a file for each patient comprised of a plurality of data records. The system also includes a processor which is coupled to a video display and which controls display information of the video display. A memory is coupled to the processor for storing display and other data. An input unit, which may include a keyboard or a cursor control device, is also coupled to the processor. The processor performs arithmetic and logic operations as may be directed by a computer program, accesses the memory to obtain display data and displays data on the video display. The display data includes a timeline representing the time period spanned by data records in a selected data file which may be accessed.

In response to signals from the cursor control device, a cursor is positioned on the display. This cursor is positioned on the timeline to indicate a desired date and time. The cursor control device provides signals indicative of its position on the timeline which the processor uses to determine a desired date and time. Responsive to this determination of the desired date and time, the processor accesses at least one data record from the data file for a selected patient corresponding to the desired date and time. The accessed data records may have time stamps within a certain range from the desired date and time. The accessed data records are then displayed on the video display.

BRIEF DESCRIPTION OF THE DRAWING

In the drawing,

FIG. 3 is a graphical illustration of a display where the length of stay of a patient in a hospital is short;

FIG. 4 is a graphical illustration of a display where the length of stay of a patient in a hospital is medium;

FIG. 5 is a graphical illustration of a display where the length of stay of a patient in a hospital is long;

DETAILED DESCRIPTION

Figure 1:
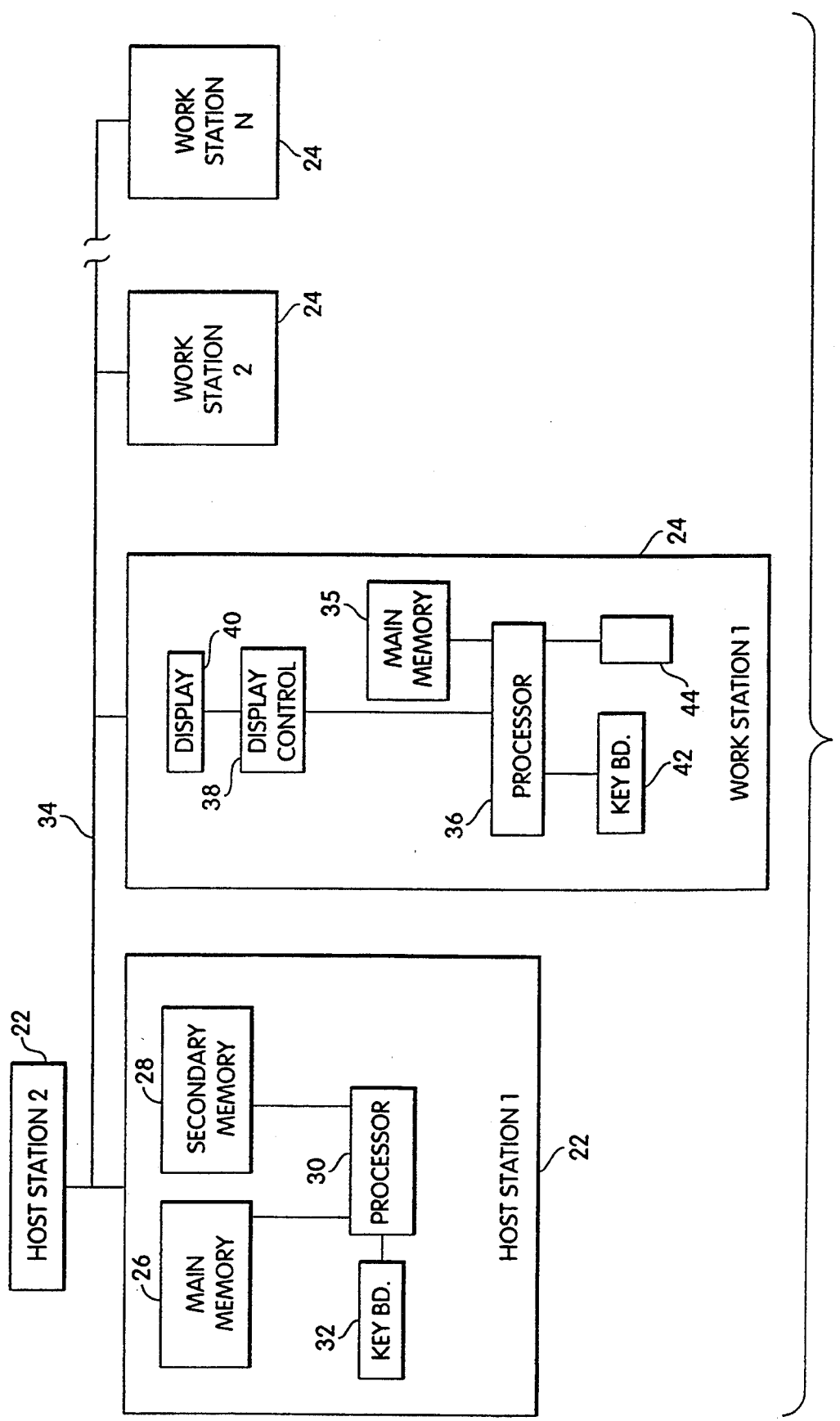
FIG. 1 is a block diagram of a data processing system suitable for an embodiment of the present invention.

A data processing system 20, suitable for implementing a display system for a medical information system in accordance with the present invention, is illustrated in FIG. 1. The data processing system 20 includes at least one host station 22 and one or more workstations 24. A host station 22 includes a main memory 26 for holding data which may be used by users of the system. A secondary memory 28 is also provided for maintaining the integrity of the database. A processor 30 is provided for reading and writing of data from the database stored in memory 26, and for executing other operations requested by users at other host stations 22, at workstation 24 and/or at input unit 32, such as a keyboard 32, for the host station. It is preferable to have a second host station 22 to provide a redundant database in case of failure of the first host station. The host stations are normally and preferably located at a central location within a hospital or other health care facility. Workstations 24, on the other hand, are normally located within a care unit in the hospital and are connected to the host stations via a network 34.

Workstation 24 normally includes a main memory 35 for storing local copies of data and programs and a processor 36 which is capable of performing read and write requests for data from its main memory, and performing other operations as directed by a computer program, such as logical and arithmetic operations, on data. The processor 36 also controls a display control 38 for controlling display of information on a monitor 40 or other video display. The workstation 24 also includes an input unit, such as a keyboard 42 and a cursor control device 44, such as a mouse or a trackball. Preferably, a trackball with a plurality of switches is used as the cursor control device. Workstations 24, interconnected by network 34, are provided for a care unit, with a workstation 24 preferably being provided for each patient room in a hospital or health care facility in the preferred embodiment.

In the preferred embodiment at the time of filing this application, the workstations were implemented as HP-Apollo 9000 computers, model 710; host stations were implemented using model 730 of the same computer. These computers were interconnected by an I.E.E.E. 802.3 network, and were provided with the HP-UX operating system version 9.0. It should be understood that the invention is not limited by the specific computers, network and operating system shown and described. Other data processing systems may be used in connection with a database to practice this invention. Such a system may be programmed to embody the present invention, such as by using the HP-C++ programming language and its corresponding HP-C++ compiler, version 2.34. It should be understood that many other programming languages and compilers are available for this purpose and the invention is not limited thereby.

The computer display system and method of the present invention is used in a medical information system which includes a database of patient information, as in a hospital information system. In one embodiment of the invention, each data record in the database for a patient has a time and date stamp. Such data records may include vital sign information, urine and blood sample analysis results, treatments provided, etc. The database is preferably a relational database, wherein each record is related to a single patient, allowing access to the data by reference to the patient name, among other things.

The invention is not limited to time-stamped information. The system need only provide sufficient information so that an indication of the duration of a patient's stay in the health care facility can be determined. The following description is based on an example of a database having time-stamped data records of patient information.

FIGS. 2-5 illustrate suitable graphics for placement on display 40 for use in a computer display system in accordance with the present invention. Similar reference numbers in the figures indicate similar elements. The location of the graphics on the display 40 is not material to this invention; however it may be preferable to fill the display with the graphics. Such graphics include a data sheet 52 which may be displayed in the same manner as in the HP CareVue 9000 System.

The data sheet 52 is made up of a number of columns 70. Each column 70 represents a specific date and time or a period of time. The period of time represented by each column may variable and user-selectable. In each column 70, data records are presented in rows 72, wherein each row corresponds to a given type of patient information. Where a data record is found at the intersection of a row and column, the data sheet indicates that the recorded information was obtained at the date and time or during the period of time specified for the indicated column. Each column is preferably labeled with its corresponding date and time or time period.

Figure 2:
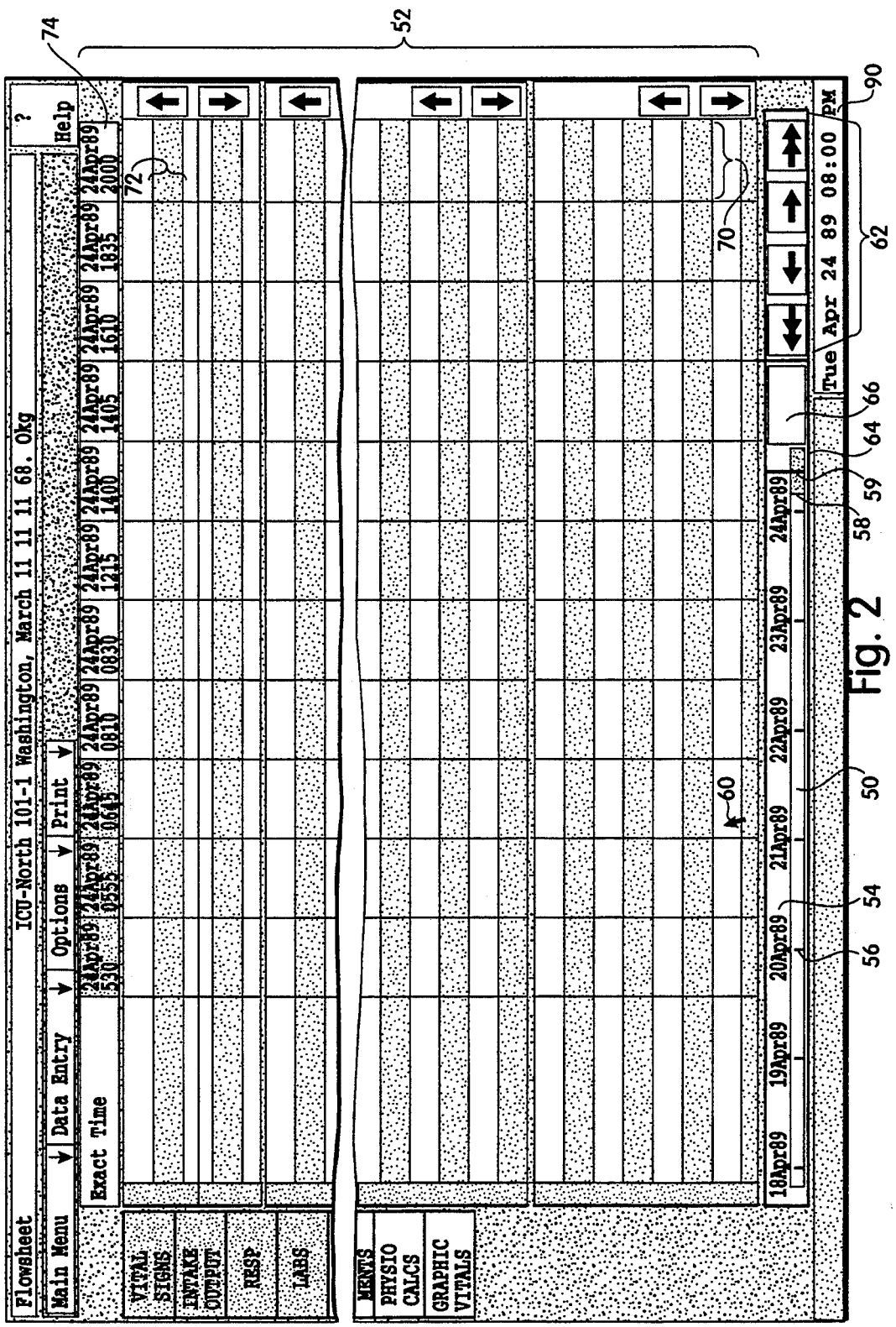
FIG. 2 is a graphical illustration of a display for a display system in accordance with the present invention.

The graphics of FIG. 2 also include a box 64 which contains a length-of-stay (LOS) timeline 50 and a clock 66. The box 64 has a border which may be thick or thin depending on the state of the system. In this figure, box 64 is beneath the data sheet 52. The location and orientation of this box within the graphics are not limited to the location and orientation shown. Nonetheless, it is preferable to provide a display configuration which is intuitive. Thus, if the data records are displayed in the data sheet 52 with earliest data records at the left and more recent data records to the right, for example, the box 64 should have its earliest time at the left and current time at the right. Alternatively, data records and box 64 could be arranged vertically if so desired.

The LOS timeline 50 represents an approximation of the duration of a patient's stay in a care unit or hospital, starting with an approximate admission time to the care unit or hospital and ending with an approximation to the earlier of either transfer or discharge from the care unit or hospital, or the current time (if the patient has not been discharged). The approximate admission date and time is determined by the earliest time stamp of all information for the patient in the database. The duration of a patient's stay is approximated by the difference between the earliest date and time stamp of the data records for the patient and either the current time or, if the patient has been discharged, the latest date and time stamp of the data records for the patient. These records for the patient may be found using conventional data searching and comparison techniques. The timeline 50 therefore is also representative of the time period covered by data records in the data file for the patient.

On the display, the approximate admission time can be indicated by either end of the LOS timeline 50, but is preferably indicated by the end closest to the earliest displayed data records. Because data is not necessarily entered the moment the patient enters the care unit or hospital, the approximate admission date and time is often not the admission date and time written in the patient's admission record, unless the admission date and time is itself a data record in the data file for the patient. If different care units in a hospital are served by different computer systems which are not interconnected, the approximate admission time for a patient also may vary between care units.

The LOS timeline 50 preferably has a label 54 and tick-mark 56 for each day of a patient's stay. The tick mark 56 is preferably placed on the timeline 50 at a location representing the beginning of each day of the stay for the patient. Each day may have a tick mark 56 on the LOS timeline 50, depending on the actual duration of the stay. Each label 54 preferably has the same size, font and format as labels in the data sheet 52. A label 54 is preferably centered on a corresponding tick mark 56. A labeled tick mark 56 is made thicker than an unlabeled tick mark to help associate the label 54 with it. The tick mark for the first day of the LOS timeline 50 is preferably always labeled.

A marker 58 highlights, on the LOS timeline 50, the time period represented by any currently displayed data on the data sheet 52. The length of the marker is determined by mapping the period of time covered by displayed data records into the graphical space defined for the timeline. In the center of the marker 58 is a vertical bar 59 which corresponds to the center column of the displayed data sheet 52. This bar 59 also may be used to indicate the first or last data record shown on the data sheet 52 and may be placed accordingly on the marker 58. This vertical bar 59 indicates to the user that the display columns on the data sheet 52 will be centered around the vertical bar position.

Figure 3:
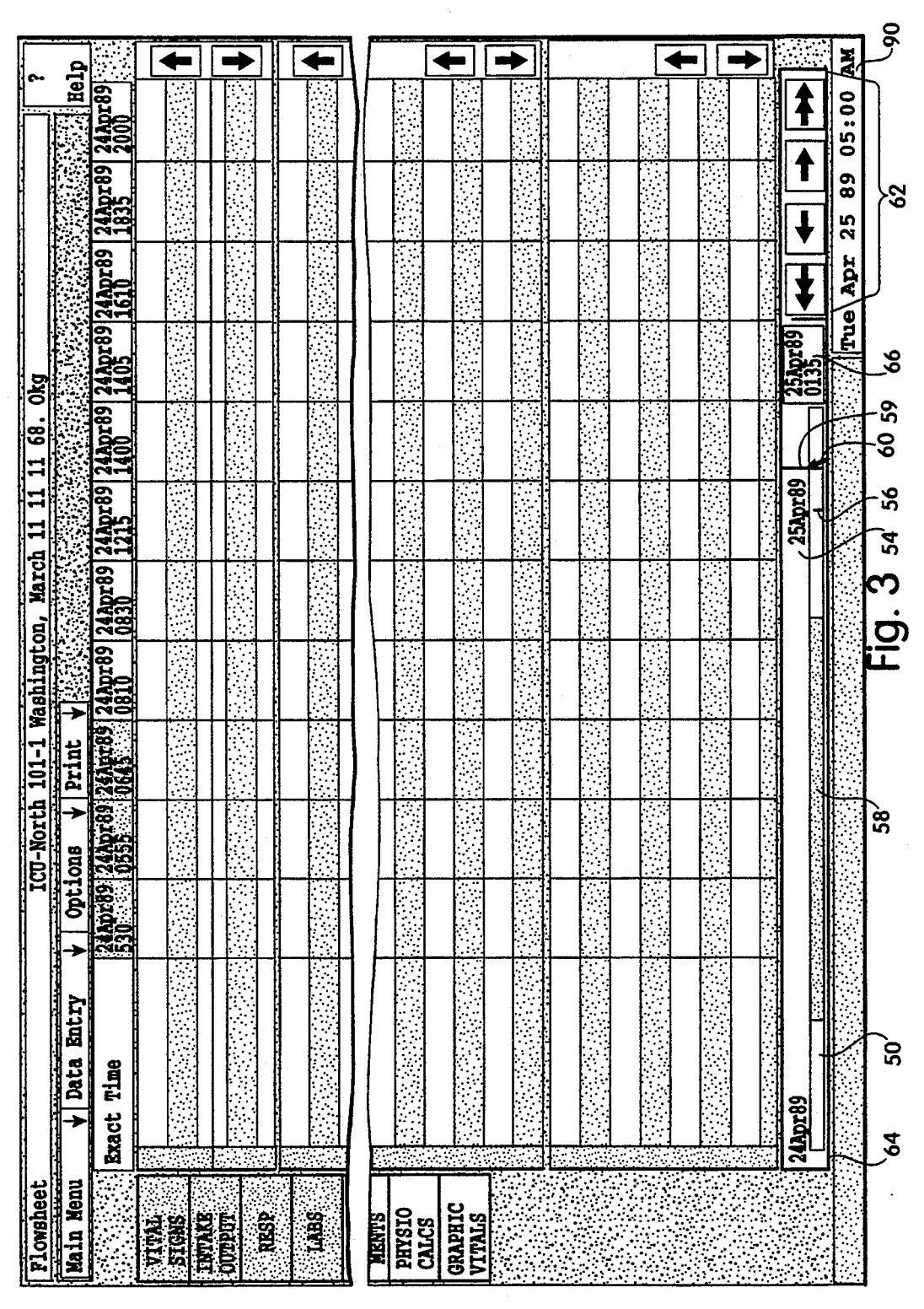

Because the LOS timeline 50 always represents the length of stay, regardless of its duration, the LOS timeline 50 has to accommodate a length of stay as short as one minute, and as long as several months. For this purpose, there may not be any, or merely few, tick marks 56 on an LOS timeline for a short length of stay. For example, as shown in FIG. 3, the length of stay is only a day and a few hours. Only two tick marks are used. The marker 58 may occupy nearly the entire LOS timeline.

Figure 4:
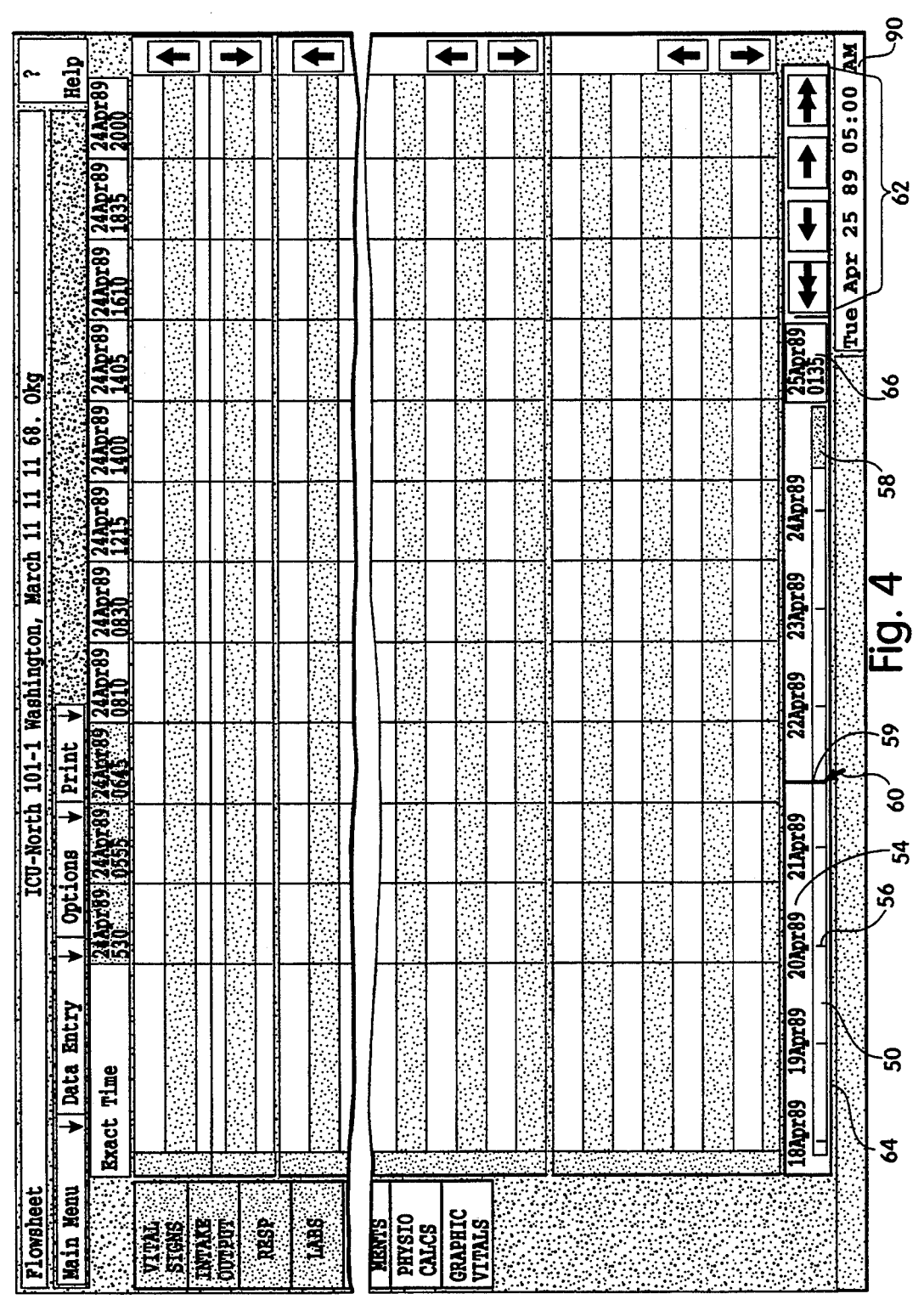

For a medium length of stay, for example less than about seven days, a tick mark 56 and label 54 may be used for each day, such as shown in FIGS. 2 and 4. With this arrangement there is often enough space between tick marks to provide resolution down to an hour. In this case, the marker 58 occupies only a portion of the LOS timeline 50.

Figure 5:
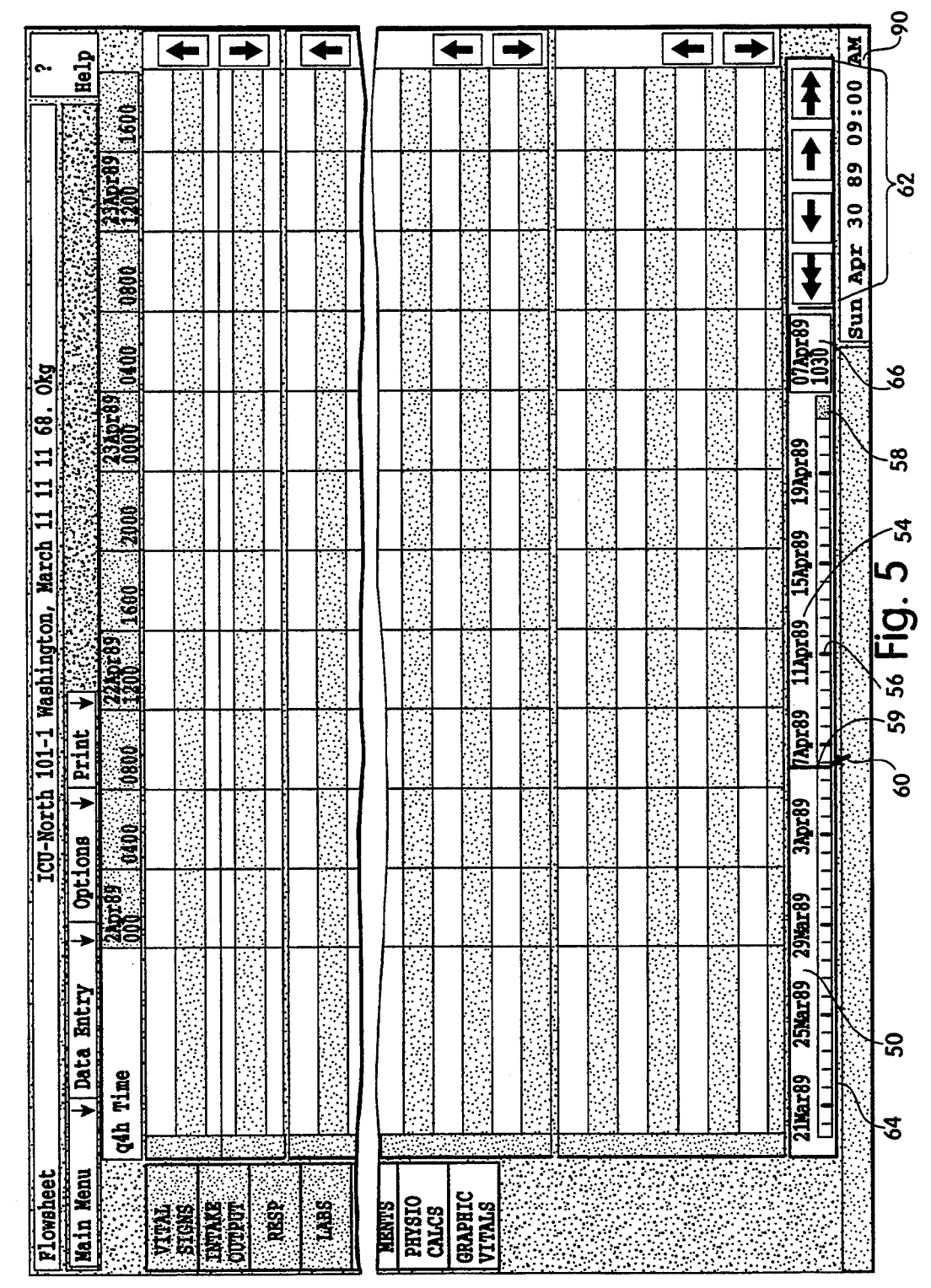

As the duration length of the stay increases, as shown in FIG. 5, the spacings between tick marks 56 on the LOS timeline 50 are compressed, thus providing less time resolution. The frequency of occurrence (per number of days) of tick marks 56 and labels 54 also decreases. Since a minimum space is preferably maintained between tick marks 56 and labels 54 to maintain readability, as the LOS timeline is compressed further tick marks 56 and labels 54 are removed. Depending on the pixel count and size of the graphics on the display, the number of tick marks may be determined. For example, for a duration of a stay of about nine to 16 days, every two days may be labeled using the data processing system described and shown in FIG. 1; for a duration of a stay of about 17-24 days, every three days may be labeled; and for a duration of a stay of about 25-32 days, every four days may be labeled.

The number and frequency of tick marks are reduced every 40 days. That is, one tick mark 56 is provided every two days when the duration of a stay is about 40-80 days, whereas, one tick mark 56 is provided for every three days when the duration of a stay is about 81-120 days.

Arrow key boxes 62 may also be provided in the graphics, as in the CareVue 9000 system, to facilitate searching for an exact time once a general location in the data file has been selected using the LOS timeline 50. Single left and right arrows may be selected using the cursor control device to access any immediately earlier or later data records for a patient than those already displayed. The double left and right arrows are used to obtain the immediately earlier or later screen full of data. These boxes have a border which may be thick or thin depending upon the state of the system.

A clock 66 shows a date and time represented by the relative position of the cursor on the LOS timeline 50. The distance (in pixels) between the cursor and the beginning of the LOS timeline, divided by the length of the LOS timeline (in pixels), multiplied by the duration represented by the LOS timeline, and added to the admission date and time gives the time and date to be shown by the clock 66. This clock uses the same date and time format that is used to label the time columns in data sheet 52. The use of this clock 66 provides a user with an indication of the time indicated by the cursor position on the LOS timeline 50.

Figure 6:
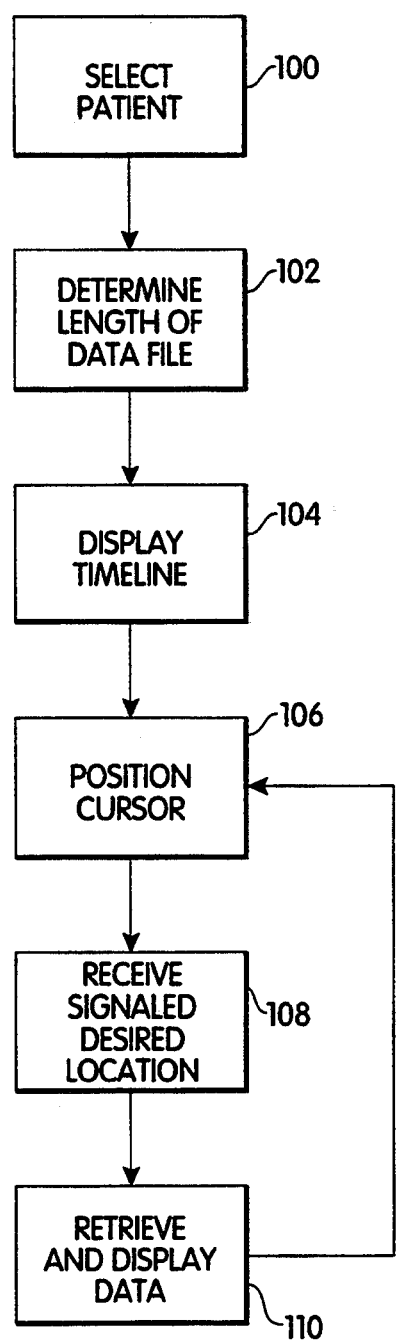
FIG. 6 is a flow chart describing how the invention may be used to access data.

Referring now to the flow chart of FIG. 6, the use of this display system to access data records from a data file will now be described. A user first selects a data file, step 100, such as by selecting a patient name and indicates the computer of the selected patient using the input device. In response, the computer selects the data file from the database corresponding to the selected patient. The computer then determines the duration of the stay of the patient based on data records in the patient's data file in step 102. For example, the first and last data records are examined to determine the difference between their time stamps in order to provide an indication of the time period covered by the data records and the data file. As mentioned above, in a hospital information system, a field is often provided for each data file for a patient to indicate whether the patient is discharged. The step 102 of determining the duration of the patient's stay may include examining this field. If it is determined that the patient was discharged, the last data record is examined to determine the duration of the patient's stay. Otherwise, the current time is used to determine the duration.

An LOS timeline, indicative of the duration of the patient's stay is then displayed in step 104. The duration is mapped to the space provided for the timeline as part of the graphics on display 40. An appropriate number of tick marks and labels can be placed on the timeline, dependent on the duration of the stay as described above.

A user manipulates an input unit, e.g., maneuvers a cursor control device 44 (FIG. 1) such as the trackball described above, in response to which the computer positions the cursor 60 on the display 40 (step 106). The distance (in pixels) between the cursor position and the beginning of the LOS timeline, divided by the length of the LOS timeline (in pixels) is multiplied by the duration represented by the LOS timeline. This product is added to the admission date and time (e.g., the time of the first data record). This time is then displayed in the clock 66, which is changed while the cursor position changes. If the cursor position is beyond the left or right edges of the LOS timeline, but still within the box 64, the corresponding boundary time (either earliest or latest) for the timeline is shown on the clock 66.

When the cursor is at a point on the displayed LOS timeline 50 which corresponds to a desired date and time, the user depresses a switch, such as is typically found on suitable trackball devices, a signal from which is received by the computer (step 108). In response, the computer retrieves and displays the data corresponding to the desired date and time (step 110).

In order to retrieve data, the computer determines, in the same manner as the time for the clock 66 is determined, the desired date and time based on the cursor position at the time the switch is depressed. The computer then accesses the data record corresponding to the indicated date and time from the data file for the selected patient using well-known data access techniques. The data sheet 52 may then be re-displayed with the center column having new data records corresponding to the selected user time. The marker 58 is placed at the indicated location on the LOS timeline 50 and the vertical bar 59 is placed at the selected cursor location. The provision of this feature thus allows a user to find quickly data records for a specific date and time in the database.

In response to movement of the cursor and activation of switches, the computer may also perform a number of functions to facilitate selection of a desired date and time. For example, when the cursor is moved into the box 64, as may be detected using conventional techniques the border of the box may be thickened to indicate that the box is activated.

In a preferred embodiment, the marker 58 may also be made to disappear and the vertical bar 59 to appear on the LOS timeline 50 at the cursor location. If the cursor is at either end of the box 64 where it is not over the LOS timeline 50, the vertical bar 59 is placed at the corresponding end of the LOS timeline 50. The correct location of the vertical bar is maintained by comparing it to the start and end times represented by the timeline. The clock 66 may show the date and time corresponding to the position of the vertical bar 59, and the marker 58 does not move. While the cursor is moved along the LOS timeline 50, the vertical bar 59 is at exactly the same point as the cursor position and tracks the cursor as it moves along the LOS timeline. When the cursor is moved out of the box 64, the border of box 64 returns to its normal width and the clock 66 is made blank. The blanking of the clock is provided solely to reduce potential confusion with the actual date and time, which is also typically displayed such as at 90.

Figure 7:
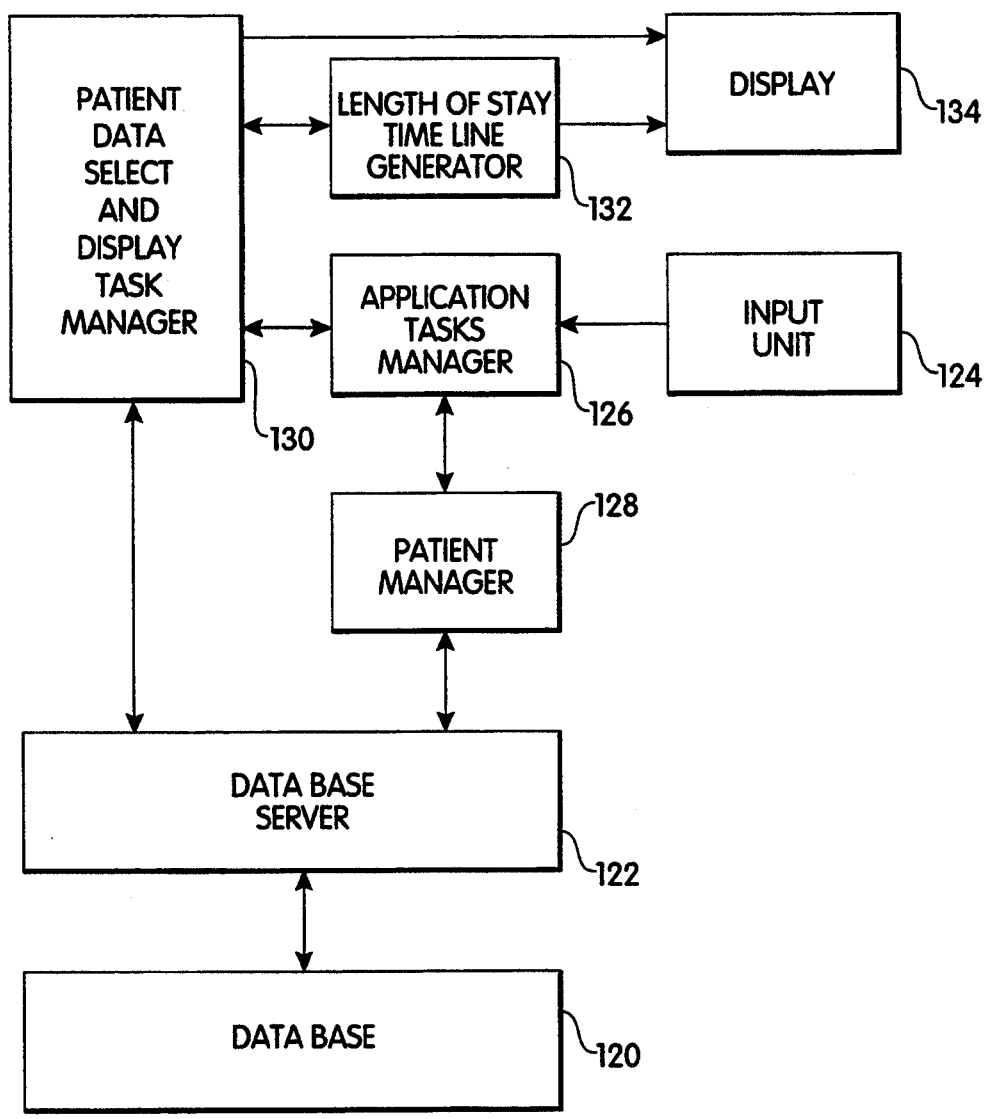
FIG. 7 is a data flow diagram illustrating relationships between modules of a system in accordance with the invention.

An embodiment of the invention will now be described in the context of a data flow diagram as represented in FIG. 7. A database 120 stores patient information and is the database stored in the host station 22 and other host stations in the data processing system 20 (FIG. 1). Also in the host station 22 is a database server 122 (FIG. 7) which controls access to the database 120. An input unit 124 (FIG. 7), such as keyboard 42 and cursor control device 44 (FIG. 1) allow a user to provide input to an application task manager 126 running on a workstation 24 (FIG. 1), which is an application program suitable for entering and viewing data in the database 120. A patient manager 128 controls the input of patient data to the database 120. If a user indicates, using input unit 124, that viewing of patient data is desired, the application task manager 126 sends such information to the patient data select and display task manager 130. Given the user's input, the patient data select and display task manager 130 determines, using methods described above, which data in the patient database 120 to access. The patient data select and display task manager 130 also provides information to a length of stay time line generator 132 which determines, using methods described above, what the length of stay time line should look like for a selected patient. The length of stay time line generator 132 and the patient data select and display task manager 130 provide the appropriate display information to a display 134 which includes the display control 38 and display 40 of the workstation 24 (FIG. 1).

Having now described an embodiment of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims.

What is claimed is:

1. A computer-implemented method for facilitating access to patient information in a medical information system for a health care facility, the medical information system including a computer with an input unit, a video display and a database containing a data file of a plurality of data records for at least one patient staying in the health care facility, the method comprising the steps of:

receiving a first input from the input unit which identifies a patient for which a data file is to be accessed;

determining, on the basis of data records in the data file for the identified patient, a duration of the stay in the health care facility of the identified patient;

displaying on the video display a line having a length and being representative of the determined duration of the stay of the identified patient in the health care facility;

receiving a second input from the input unit, which indicates a position on the displayed line; and accessing and displaying one of said data records from the data file for the identified patient according to the position on the displayed line indicated by the second input.

2. The method of claim 1, wherein each data record in the data file has a date and time stamp, wherein the step of determining the duration of the stay of the identified patient includes the step of determining a time period between the earliest and latest data records in the data file for the identified patient.

3. The method of claim 1 wherein the displayed line has a fixed length for any determined duration and the method includes the step of mapping the determined duration to the fixed length.

4. The method of claim 1, wherein each data record in the data file has a date and time stamp, wherein the step of determining the duration of the stay of the identified patient includes the step of determining a time period between the earliest record in the data file for the identified patient and a current time.

5. The method of claim 2 wherein the step of displaying a line includes the step of displaying a line having at least one label which identifies a date for which a data record in the data file for the identified patient has a corresponding date stamp.

6. The method of claim 4 wherein the step of displaying a line includes the step of displaying a line having at least one label which identifies a date for which a data record in the data file for the identified patient has a corresponding date stamp.

7. The method of claim 1 wherein the step of displaying a line includes the step of displaying a line having a marker which identifies a time period corresponding to currently displayed data records.

8. The method of claim 1 wherein the step of displaying a line includes the step of displaying a line having a bar which identifies the time and date of any data record displayed at a center of any currently displayed data.

9. The method of claim 1 wherein the step of displaying a line includes the steps of displaying a line representing time and displaying a clock which identifies the time corresponding to a position of a cursor on the line.

10. A computer display system for facilitating access to patient information in a medical information system for a health care facility, the medical information system including a database containing a data file of a plurality of data records for at least one patient staying in the health care facility, the system comprising:
  a processor;
  a memory coupled to the processor for storing display data;
  a video display coupled to the processor;
  an input unit coupled to the processor, at least for providing signals indicative of a desired cursor location on the video display;
  the processor including:
    means, responsive to a signal from the input unit, for identifying a data file for a patient whose data records are to be accessed;
    means for displaying on the video display a line having a length and being representative of a duration of a stay in the health care facility of the patient whose data records are to be accessed;
    means, responsive to signals from the input unit, for positioning a cursor on the video display and for selecting a data record from the data file according to a position of the cursor on the displayed line; and
    means, responsive to a selection of one of said data records, for accessing and displaying on the video display the selected data record from the data file for the identified patient.

11. The computer display system of claim 10 wherein the data file includes a plurality of data records, each data record having a time and date stamp, and wherein the means for displaying the line on the video display includes means for determining a time period between the earliest and latest data records in the identified data file.

12. The computer display system of claim 10 wherein the displayed line has a fixed length for any determined length of the identified data file and the system includes means for mapping the determined duration to the fixed length.

13. The computer display system of claim 10 wherein a data file includes a plurality of data records, wherein each data record has a date and time stamp, wherein the means for displaying a line includes means for determining the time period between the earliest record in the identified data file and a current time.

14. The computer display system of claim 11 wherein the means for displaying a line includes means for displaying a line having at least one label which identifies a date for which a data record in the data file for the identified patient has a corresponding date-stamp.

15. The computer display system of claim 13 wherein the means for displaying a line includes means for displaying a line having at least one label which identifies a date for which a data record in the data file for the identified patient has a corresponding date-stamp.

16. The computer display system of claim 10 wherein the means for displaying a line includes means for displaying a line having a marker which identifies a time period corresponding to currently displayed data records.

17. The computer display system of claim 10 wherein the means for displaying a line includes means for displaying a line having a bar which identifies the time and date of any data record displayed at the center of any currently displayed data.

18. The computer display system of claim 10 wherein the means for displaying a line includes means for displaying a line representing time and for displaying a clock which identifies the time corresponding to the cursor position on the line.

19. A computer-implemented process for facilitating access to patient information in a medical information system for a health care facility which includes a computer having an input unit, a video display and a database containing a data file of a plurality of data records for at least one patient staying in the health care facility, the process, implemented in the computer, comprising the steps of:
  identifying a data file for a patient whose data records are to be accessed;
  determining, on the basis of data records in the identified data file, a duration of a stay in the health care facility of the patient whose data records are to be accessed;
  displaying on the video display a representation of the determined duration;
  positioning a cursor on the displayed representation in response to a signal from the input unit;
  accessing, in response to a signal from the input unit, a data record from the identified data file according to a position of the cursor on the displayed representation; and
  displaying the data record.

20. The method of claim 19, wherein each data record in the data file has a date and time stamp, wherein the step of determining the duration of the stay of the identified patient includes the step of determining a time period between the earliest and latest data records in the data file for the identified patient.

21. A data processing system for facilitating access to patient information in a medical information system for a health care facility, the medical information system including a database containing a data file of a plurality of data records for at least one patient staying in the health care facility, the data processing system comprising:
- a video display;
- an input unit, at least for providing signals indicative of a desired cursor location on the video display;
- a length of stay time line generator connected to the display for generating and displaying on the video display a line having a length and being representative of the duration of the stay in the health care facility of a patient whose data records are to be accessed;
- an application task manager connected between the input unit and the patient data select and display task manager and responsive to the signal from the input unit for identifying a data file for a patient whose data records are to be accessed; and
- a patient data select and display task manager connected to the length of stay time line generator, the video display and the application task manager and responsive to the signal from the input device to correlate a position of the cursor on the displayed line with one of said data records and for accessing the data record.

22. A computer-implemented method for facilitating access to patient information in a medical information system for a health care facility, the medical information system including a computer with an input unit, a video display and a database containing a data file of a plurality of data records for at least one patient staying in the health care facility, the method comprising the steps of:
- displaying on the video display a graphical representation of the duration of a stay of the patient;
- receiving a signal indicative of a position on the displayed graphical representation;
- correlating the position on the displayed graphical representation to a data record in the data file for the patient; and
- accessing one of said data records correlated to the position.

* * * * *